United States Patent
Hamelmann et al.

(10) Patent No.: US 11,559,276 B2
(45) Date of Patent: Jan. 24, 2023

(54) SYSTEMS AND METHODS FOR ULTRASOUND SCREENING

(71) Applicant: KONINKLIJKE PHILIPS N.V., Eindhoven (NL)

(72) Inventors: Paul Christoph Hamelmann, Aachen (DE); Alexander Franciscus Kolen, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 17/052,417

(22) PCT Filed: Apr. 25, 2019

(86) PCT No.: PCT/EP2019/060648
§ 371 (c)(1),
(2) Date: Nov. 2, 2020

(87) PCT Pub. No.: WO2019/211171
PCT Pub. Date: Nov. 7, 2019

(65) Prior Publication Data
US 2021/0059634 A1  Mar. 4, 2021

(30) Foreign Application Priority Data

May 2, 2018  (EP) .................................... 18170374
Oct. 15, 2018  (EP) .................................... 18200425

(51) Int. Cl.
*A61B 8/08* (2006.01)
*A61B 8/00* (2006.01)
*A61B 8/02* (2006.01)

(52) U.S. Cl.
CPC .............. *A61B 8/0866* (2013.01); *A61B 8/02* (2013.01); *A61B 8/0883* (2013.01);
(Continued)

(58) Field of Classification Search
CPC .... A61B 2562/0219; A61B 2562/0261; A61B 8/02; A61B 8/085; A61B 8/0866;
(Continued)

(56) References Cited

U.S. PATENT DOCUMENTS 5,123,420 A  6/1992 Paret
5,997,479 A  12/1999 Savord
(Continued)

FOREIGN PATENT DOCUMENTS

WO  2012017364 A1  2/2012
WO  2017045915 A1  3/2017
WO  2017194392 A1  11/2017

OTHER PUBLICATIONS

International Search Report and Written Opinion, International Application No. PCT/EP2019/060648, dated Aug. 6, 2019.
(Continued)

*Primary Examiner* — Yi-Shan Yang
*Assistant Examiner* — Alexei Bykhovski

(57) ABSTRACT

The invention provides an ultrasound system including an ultrasound transducer array and a processor. The ultrasound transducer array comprises a plurality of transducer elements adapted to conform with a subjects body. Further, at least two ultrasound transducer elements of the plurality of transducer elements are adapted to acquire a plurality of ultrasound signals from a region of interest at different orientations relative to said region of interest. The processor is adapted to receive ultrasound signals acquired by the ultrasound transducer array. The processor is further adapted to partition the plurality of ultrasound signals according to a signal depth and, for each ultrasound signal partition, calculate a Doppler power. For each ultrasound signal, the processor identifies a depth of a fetal heartbeat based on the Doppler power of each ultrasound signal partition and
(Continued)

identifies a fetal heart region based on the identified fetal heartbeat and a location of the at least two ultrasound transducers.

11 Claims, 6 Drawing Sheets

(52) U.S. Cl.
CPC .......... *A61B 8/4263* (2013.01); *A61B 8/4494* (2013.01); *A61B 8/488* (2013.01); *A61B 2562/0219* (2013.01); *A61B 2562/0261* (2013.01)

(58) Field of Classification Search
CPC ... A61B 8/0883; A61B 8/4227; A61B 8/4236; A61B 8/4254; A61B 8/4263; A61B 8/4272; A61B 8/4455; A61B 8/4477; A61B 8/4494; A61B 8/469; A61B 8/483; A61B 8/488; A61B 8/5207
See application file for complete search history.

(56) References Cited

U.S. PATENT DOCUMENTS

| | | | |
|---|---|---|---|
| 6,013,032 A | 1/2000 | Savord | |
| 6,283,919 B1 | 9/2001 | Roundhill | |
| 6,443,896 B1 | 9/2002 | Detmer | |
| 6,458,083 B1 | 10/2002 | Jago | |
| 6,530,885 B1 | 3/2003 | Entrekin | |
| 6,623,432 B2 | 9/2003 | Powers | |
| 7,470,232 B2 | 12/2008 | Hoctor | |
| 2003/0210175 A1* | 11/2003 | Bickert | G01S 7/2927 342/93 |
| 2005/0020918 A1* | 1/2005 | Wilk | A61B 5/6804 600/439 |
| 2011/0172540 A1 | 7/2011 | Jackson | |
| 2013/0331704 A1* | 12/2013 | Salzman | A61B 8/0866 600/459 |
| 2016/0270670 A1* | 9/2016 | Oz | A61B 5/282 |
| 2017/0224268 A1* | 8/2017 | Altini | A61B 5/4356 |
| 2018/0125460 A1* | 5/2018 | Perrey | A61B 8/13 |

OTHER PUBLICATIONS

Hamelmann, P. et al., "Flexible sensor matrix with dynamic channel weighting for improved estimation of the fetal heart rate by doppler ultrasound", 2017, IEEE International Ultrasonics Symposium.

Hamelmann, P. et al., "Improved ultrasound transducer positioning by fetal heart location estimation during doppler based heart rate measurements", Physiol. Meas. 38 (2017).

* cited by examiner

SYSTEMS AND METHODS FOR ULTRASOUND SCREENING

This application is the U.S. National Phase application under 35 U.S.C. § 371 of International Application No. PCT/EP2019/060648, filed on 25 Apr. 2019, which claims the benefit of European Application Serial No. 18170374.5, filed 2 May 2018 and European Application Serial No. 18200425.9, filed 15 Oct. 2018. These applications are hereby incorporated by reference herein.

FIELD OF THE INVENTION

The invention elates to the field of ultrasound, and in particular to the field of fetal ultrasound screening.

BACKGROUND OF THE INVENTION

The increasing use of assisted reproductive technology due to increasing maternal age has led to a significant increase in the number of twin births. Twin pregnancies are associated with higher risk and, therefore, regular monitoring of fetal health is crucial. Fetal health is typically assessed by measuring the fetal heart rate using a Doppler ultrasound transducer. In twin pregnancies, two independent ultrasound transducers need to be manually positioned on the maternal abdomen, which requires skill and experience.

Clinical problems experienced during the measurement of twin fetal heartrates may be caused because both hearts lie in the same measurement range of one transducer. The measured Doppler signals then contain information relating to the hearts of both fetuses and the fetal heart rate estimation algorithm fails to extract the correct fetal heart rate information for either fetus.

Further, it is possible that both transducers may be mistakenly oriented towards the same fetal heart and measure the same heart rate, thereby missing the heart rate information of the other fetus. This may result in potential problems with one of the fetuses being missed entirely. The heart locations may also change over time due to fetal movement and repositioning of the ultrasound transducers may be required, thereby introducing additional uncertainty to the measured fetal heart rates.

In addition, it is possible that both ultrasound transducers are positioned correctly, but the heart rates coincidentally coincide. In this case, the system may not be able to distinguish whether both measured heart rates belong to the same fetus or are from two different Doppler sources. Further, it is possible that registration of the maternal heart rate may occur, rather than the heart rates of one or more of the fetuses, because a pulsating maternal artery is located within the measurement volume.

There is therefore a need for a system to more reliably acquire heartrate information from multiple fetuses without the need for significant additional hardware.

SUMMARY OF THE INVENTION

The invention is defined by the claims.

According to examples in accordance with an aspect of the invention, there is provided an ultrasound system, the system comprising:
an ultrasound transducer array, wherein the ultrasound transducer array comprises a plurality of transducer elements, adapted to conform with a subject's body and wherein at least two ultrasound transducer elements of the plurality of transducer elements are adapted to acquire a plurality of ultrasound signals from a region of interest at different orientations relative to said region of interest; and
a processor adapted to receive ultrasound signals acquired by the ultrasound transducer array, wherein the processor is adapted to:
partition the plurality of ultrasound signals according to a signal depth;
for each ultrasound signal partition, calculate a Doppler power;
for each ultrasound signal, identify a depth of a fetal heartbeat based on the Doppler power of each ultrasound signal partition; and
identify a fetal heart region based on the identified fetal heartbeat and a location of the at least two ultrasound transducers.

This system allows for a fetal heartbeat to be located with greater accuracy, particularly in the case of multiple fetal hearts (twins) or of a maternal blood vessel being captured within the ultrasound signal.

The Doppler power reflects the total motion within a given measurement volume, or sample volume. The signal depth, used to partition the ultrasound signals, determines the depth of this sample volume. The shape of the transmitted ultrasound beam determines the length and width of the sample volume. Using the known positions (locations) of the transducers, the location of the sample volume within the imaging area may be determined.

Typically, the sample volumes having the strongest Doppler powers are indicative of the location of the fetal heart(s). 3D visualization further clarifies the location and any further Doppler sources within the imaging region (such as a maternal blood vessel).

The use of an array adapted to simply fit the form of the subject reduces, or eliminates, the need for the clinician to perform the complex task of correctly positioning, in the case of twins, two ultrasound probes to acquire the two fetal heartbeats.

In an embodiment, the calculation of the Doppler power comprises:
calculating a Doppler signal based on the ultrasound signal partition; and
calculating a mean squared value for the Doppler signal over a predetermined time period, thereby calculating the Doppler power.

In a further embodiment, the time period is greater than or equal to 1 second, for example greater than or equal to 2 seconds.

In this way, the risk of missing a heartbeat within the measurement window is reduced, or eliminated.

In an arrangement, the identifying of the depth of the fetal heartbeat comprises comparing the Doppler power to a threshold power.

In this way, power values below a given value are rejected, thereby removing smaller motions due to factors other than the fetal heartbeat.

In a further arrangement, the identifying of the depth of the fetal heartbeat further comprises clustering the Doppler power values above the threshold power.

In this way, Doppler power attributed to the fetal heartbeat may be grouped together, thereby leading to an indication of a fetal heart region.

In an yet further arrangement, the clustering is performed by way of a two-component Gaussian mixture model or a k-means clustering model.

In an embodiment, the processor is further adapted to calculate a median fetal heartrate based on the fetal heartrate of the identified fetal heartbeats.

In an embodiment, the system further comprises a display, wherein the display is adapted to show the fetal heart region to a user.

In a further embodiment, the processor is further adapted to determine a location for each ultrasound signal partition within the region of interest and wherein the display is further adapted to show the fetal heart region in relation to each ultrasound signal partition.

The displaying of the fetal heart region in relation to the entire region of interest simplifies the identification for the user. Further, this may provide an indication of incorrect fetal heart region identifications, for example where a maternal blood vessel has been identified as a fetal heartbeat.

In an arrangement, the ultrasound transducer array further comprises a sensor and the processor is further adapted to determine a curvature of the ultrasound transducer array based on an output of the sensor.

By determining the curvature of the array of transducer elements, the positions and orientations of the ultrasound transducers relative to the region of interest may be known with greater accuracy.

In a further arrangement, the sensor comprises one or more of:
 a strain gauge;
 an accelerometer;
 a piezoelectric sensor; and
 a camera.

In an embodiment, the plurality of ultrasound transducers comprise one or more of:
 piezoelectric transducers; and
 CMUTs.

According to examples in accordance with an aspect of the invention, there is provided an ultrasound imaging method, the method comprising:
 acquiring, by way of at least two ultrasound transducers having different orientations to a region of interest, a plurality of ultrasound signals;
 partitioning the plurality of ultrasound signals according to a signal depth;
 for each ultrasound signal partition, calculating a Doppler power;
 for each ultrasound signal, identifying a depth of a fetal heartbeat based on the Doppler power of each ultrasound signal partition; and
 identifying a fetal heart region based on the identified fetal heartbeat and a location of the at least two ultrasound transducers.

In an arrangement, the identifying of the depth of the fetal heartbeat comprises:
 comparing the Doppler power to a threshold power; and
 clustering the Doppler power values above the threshold power.

According to examples in accordance with an aspect of the invention, there is provided a computer program comprising computer program code means which is adapted, when said computer program is run on a computer, to implement the method described above.

These and other aspects of the invention will be apparent from and elucidated with reference to the embodiment(s) described hereinafter.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE EMBODIMENTS

Figure 1:
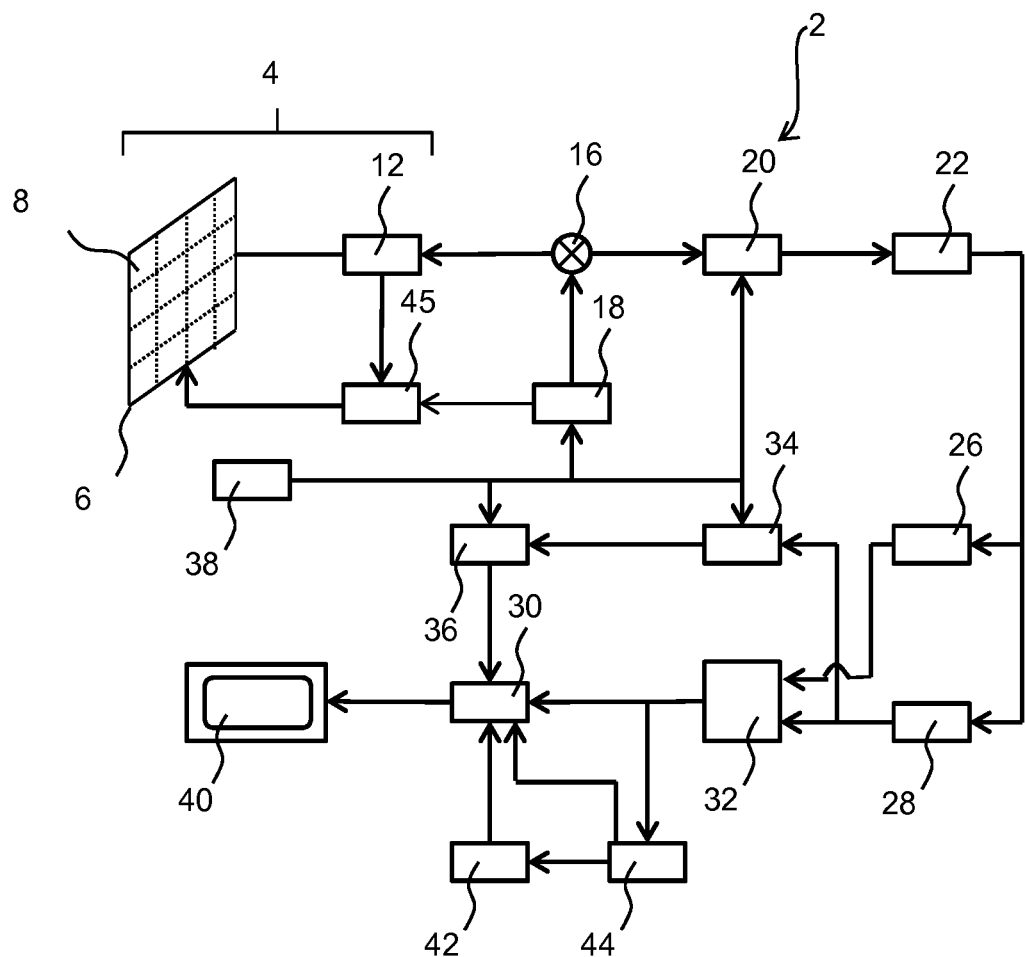
FIG. 1 shows an ultrasound diagnostic imaging system to explain the general operation.

The invention will be described with reference to the Figures.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figures are merely schematic and are not drawn to scale. It should also be understood that the same reference numerals are used throughout the Figures to indicate the same or similar parts.

The invention provides an ultrasound system including an ultrasound transducer array and a processor. The ultrasound transducer array comprises a plurality of transducer elements adapted to conform to a subject's body. Further, at least two ultrasound transducer elements of the plurality of transducer elements are adapted to acquire a plurality of ultrasound signals from a region of interest at different orientations relative to said region of interest. The processor is adapted to receive ultrasound signals acquired by the ultrasound transducer array. The processor is further adapted to partition the plurality of ultrasound signals according to a signal depth and, for each ultrasound signal partition, calculate a Doppler power. For each ultrasound signal, the processor identifies a depth of a fetal heartbeat based on the Doppler power of each ultrasound signal partition and identifies a fetal heart region based on the identified fetal heartbeat and a location of the at least two ultrasound transducers.

The general operation of an exemplary ultrasound system will first be described, with reference to FIG. 1, and with emphasis on the signal processing function of the system since this invention relates to the processing of the signals measured by the transducer array.

The system comprises an array transducer probe 4 which has a transducer array 6 for transmitting ultrasound waves and receiving echo information. The transducer array 6 may comprise CMUT transducers; piezoelectric transducers, formed of materials such as PZT or PVDF; or any other suitable transducer technology. In this example, the transducer array 6 is a two-dimensional array of transducers 8 capable of scanning either a 2D plane or a three dimensional volume of a region of interest. In another example, the transducer array may be a 1D array.

The transducer array 6 is coupled to a microbeamformer 12 which controls reception of signals by the transducer elements. Microbeamformers are capable of at least partial beamforming of the signals received by sub-arrays, generally referred to as "groups" or "patches", of transducers as described in U.S. Pat. No. 5,997,479 (Savord et al.), U.S. Pat. No. 6,013,032 (Savord), and U.S. Pat. No. 6,623,432 (Powers et al.).

It should be noted that the microbeamformer is entirely optional. Further, the system includes a transmit/receive (T/R) switch 16, which the microbeamformer 12 can be coupled to and which switches the array between transmission and reception modes, and protects the main beamformer 20 from high energy transmit signals in the case where a microbeamformer is not used and the transducer array is operated directly by the main system beamformer. The transmission of ultrasound beams from the transducer array 6 is directed by a transducer controller 18 coupled to the microbeamformer by the T/R switch 16 and a main transmission beamformer (not shown), which can receive input from the user's operation of the user interface or control panel 38. The controller 18 can include transmission circuitry arranged to drive the transducer elements of the array 6 (either directly or via a microbeamformer) during the transmission mode.

In a typical line-by-line imaging sequence, the beamforming system within the probe may operate as follows. During transmission, the beamformer (which may be the microbeamformer or the main system beamformer depending upon the implementation) activates the transducer array, or a sub-aperture of the transducer array. The sub-aperture may be a one dimensional line of transducers or a two dimensional patch of transducers within the larger array. In transmit mode, the focusing and steering of the ultrasound beam generated by the array, or a sub-aperture of the array, are controlled as described below.

Upon receiving the backscattered echo signals from the subject, the received signals undergo receive beamforming (as described below), in order to align the received signals, and, in the case where a sub-aperture is being used, the sub-aperture is then shifted, for example by one transducer element. The shifted sub-aperture is then activated and the process repeated until all of the transducer elements of the transducer array have been activated.

For each line (or sub-aperture), the total received signal, used to form an associated line of the final ultrasound image, will be a sum of the voltage signals measured by the transducer elements of the given sub-aperture during the receive period. The resulting line signals, following the beamforming process below, are typically referred to as radio frequency (RF) data. Each line signal (RF data set) generated by the various sub-apertures then undergoes additional processing to generate the lines of the final ultrasound image. The change in amplitude of the line signal with time will contribute to the change in brightness of the ultrasound image with depth, wherein a high amplitude peak will correspond to a bright pixel (or collection of pixels) in the final image. A peak appearing near the beginning of the line signal will represent an echo from a shallow structure, whereas peaks appearing progressively later in the line signal will represent echoes from structures at increasing depths within the subject.

One of the functions controlled by the transducer controller 18 is the direction in which beams are steered and focused. Beams may be steered straight ahead from (orthogonal to) the transducer array, or at different angles for a wider field of view. The steering and focusing of the transmit beam may be controlled as a function of transducer element actuation time.

Two methods can be distinguished in general ultrasound data acquisition: plane wave imaging and "beam steered" imaging. The two methods are distinguished by a presence of the beamforming in the transmission ("beam steered" imaging) and/or reception modes (plane wave imaging and "beam steered" imaging).

Looking first to the focusing function, by activating all of the transducer elements at the same time, the transducer array generates a plane wave that diverges as it travels through the subject. In this case, the beam of ultrasonic waves remains unfocused. By introducing a position dependent time delay to the activation of the transducers, it is possible to cause the wave front of the beam to converge at a desired point, referred to as the focal zone. The focal zone is defined as the point at which the lateral beam width is less than half the transmit beam width. In this way, the lateral resolution of the final ultrasound image is improved.

For example, if the time delay causes the transducer elements to activate in a series, beginning with the outermost elements and finishing at the central element(s) of the transducer array, a focal zone would be formed at a given distance away from the probe, in line with the central element(s). The distance of the focal zone from the probe will vary depending on the time delay between each subsequent round of transducer element activations. After the beam passes the focal zone, it will begin to diverge, forming the far field imaging region. It should be noted that for focal zones located close to the transducer array, the ultrasound beam will diverge quickly in the far field leading to beam width artifacts in the final image. Typically, the near field, located between the transducer array and the focal zone, shows little detail due to the large overlap in ultrasound beams. Thus, varying the location of the focal zone can lead to significant changes in the quality of the final image.

It should be noted that, in transmit mode, only one focus may be defined unless the ultrasound image is divided into multiple focal zones (each of which may have a different transmit focus).

In addition, upon receiving the echo signals from within the subject, it is possible to perform the inverse of the above described process in order to perform receive focusing. In other words, the incoming signals may be received by the transducer elements and subject to an electronic time delay before being passed into the system for signal processing. The simplest example of this is referred to as delay-and-sum beamforming. It is possible to dynamically adjust the receive focusing of the transducer array as a function of time.

Looking now to the function of beam steering, through the correct application of time delays to the transducer elements it is possible to impart a desired angle on the ultrasound beam as it leaves the transducer array. For example, by activating a transducer on a first side of the transducer array followed by the remaining transducers in a sequence ending at the opposite side of the array, the wave front of the beam will be angled toward the second side. The size of the steering angle relative to the normal of the transducer array is dependent on the size of the time delay between subsequent transducer element activations.

Further, it is possible to focus a steered beam, wherein the total time delay applied to each transducer element is a sum of both the focusing and steering time delays. In this case, the transducer array is referred to as a phased array.

In case of the CMUT transducers, which require a DC bias voltage for their activation, the transducer controller 18 can be coupled to control a DC bias control 45 for the transducer array. The DC bias control 45 sets DC bias voltage(s) that are applied to the CMUT transducer elements.

For each transducer element of the transducer array, analog ultrasound signals, typically referred to as channel data, enter the system by way of the reception channel. In the reception channel, partially beamformed signals are produced from the channel data by the microbeamformer 12 and are then passed to a main receive beamformer 20 where the partially beamformed signals from individual patches of transducers are combined into a fully beamformed signal, referred to as radio frequency (RF) data. The beamforming performed at each stage may be carried out as described above, or may include additional functions. For example, the main beamformer 20 may have 128 channels, each of which receives a partially beamformed signal from a patch of dozens or hundreds of transducer elements. In this way, the signals received by thousands of transducers of a transducer array can contribute efficiently to a single beamformed signal.

The beamformed reception signals are coupled to a signal processor 22. The signal processor 22 can process the received echo signals in various ways, such as: band-pass filtering; decimation; I and Q component separation; and harmonic signal separation, which acts to separate linear and nonlinear signals so as to enable the identification of nonlinear (higher harmonics of the fundamental frequency) echo signals returned from tissue and micro-bubbles. The signal processor may also perform additional signal enhancement such as speckle reduction, signal compounding, and noise elimination. The band-pass filter in the signal processor can be a tracking filter, with its pass band sliding from a higher frequency band to a lower frequency band as echo signals are received from increasing depths, thereby rejecting noise at higher frequencies from greater depths that is typically devoid of anatomical information.

The beamformers for transmission and for reception are implemented in different hardware and can have different functions. Of course, the receiver beamformer is designed to take into account the characteristics of the transmission beamformer. In FIG. 1 only the receiver beamformers 12, 20 are shown, for simplicity. In the complete system, there will also be a transmission chain with a transmission micro beamformer, and a main transmission beamformer.

The function of the microbeamformer 12 is to provide an initial combination of signals in order to decrease the number of analog signal paths. This is typically performed in the analog domain.

The final beamforming is done in the main beamformer 20 and is typically after digitization.

The transmission and reception channels use the same transducer array 6 which has a fixed frequency band. However, the bandwidth that the transmission pulses occupy can vary depending on the transmission beamforming used. The reception channel can capture the whole transducer bandwidth (which is the classic approach) or, by using bandpass processing, it can extract only the bandwidth that contains the desired information (e.g. the harmonics of the main harmonic).

The RF signals may then be coupled to a B mode (i.e. brightness mode, or 2D imaging mode) processor 26 and a Doppler processor 28. The B mode processor 26 performs amplitude detection on the received ultrasound signal for the imaging of structures in the body, such as organ tissue and blood vessels. In the case of line-by-line imaging, each line (beam) is represented by an associated RF signal, the amplitude of which is used to generate a brightness value to be assigned to a pixel in the B mode image. The exact location of the pixel within the image is determined by the location of the associated amplitude measurement along the RF signal and the line (beam) number of the RF signal. B mode images of such structures may be formed in the harmonic or fundamental image mode, or a combination of both as described in U.S. Pat. No. 6,283,919 (Roundhill et al.) and U.S. Pat. No. 6,458,083 (Jago et al.) The Doppler processor 28 processes temporally distinct signals arising from tissue movement and blood flow for the detection of moving substances, such as the flow of blood cells in the image field. The Doppler processor 28 typically includes a wall filter with parameters set to pass or reject echoes returned from selected types of materials in the body.

The structural and motion signals produced by the B mode and Doppler processors are coupled to a scan converter 32 and a multi-planar reformatter 44. The scan converter 32 arranges the echo signals in the spatial relationship from which they were received in a desired image format. In other words, the scan converter acts to convert the RF data from a cylindrical coordinate system to a Cartesian coordinate system appropriate for displaying an ultrasound image on an image display 40. In the case of B mode imaging, the brightness of pixel at a given coordinate is proportional to the amplitude of the RF signal received from that location. For instance, the scan converter may arrange the echo signal into a two dimensional (2D) sector-shaped format, or a pyramidal three dimensional (3D) image. The scan converter can overlay a B mode structural image with colors corresponding to motion at points in the image field, where the Doppler-estimated velocities to produce a given color. The combined B mode structural image and color Doppler image depicts the motion of tissue and blood flow within the structural image field. The multi-planar reformatter will convert echoes that are received from points in a common plane in a volumetric region of the body into an ultrasound image of that plane, as described in U.S. Pat. No. 6,443,896 (Detmer). A volume renderer 42 converts the echo signals of a 3D data set into a projected 3D image as viewed from a given reference point as described in U.S. Pat. No. 6,530,885 (Entrekin et al.).

The 2D or 3D images are coupled from the scan converter 32, multi-planar reformatter 44, and volume renderer 42 to an image processor 30 for further enhancement, buffering and temporary storage for display on an image display 40. The imaging processor may be adapted to remove certain imaging artifacts from the final ultrasound image, such as: acoustic shadowing, for example caused by a strong attenuator or refraction; posterior enhancement, for example caused by a weak attenuator; reverberation artifacts, for example where highly reflective tissue interfaces are located in close proximity; and so on. In addition, the image processor may be adapted to handle certain speckle reduction functions, in order to improve the contrast of the final ultrasound image.

In addition to being used for imaging, the blood flow values produced by the Doppler processor 28 and tissue structure information produced by the B mode processor 26 are coupled to a quantification processor 34. The quantification processor produces measures of different flow conditions such as the volume rate of blood flow in addition to structural measurements such as the sizes of organs and gestational age. The quantification processor may receive input from the user control panel 38, such as the point in the anatomy of an image where a measurement is to be made.

Output data from the quantification processor is coupled to a graphics processor 36 for the reproduction of measurement graphics and values with the image on the display 40, and for audio output from the display device (image display) 40. The graphics processor 36 can also generate graphic overlays for display with the ultrasound images. These graphic overlays can contain standard identifying information such as patient name, date and time of the image, imaging parameters, and the like. For these purposes the graphics processor receives input from the user interface (or a panel) 38, such as patient name. The user interface is also coupled to the transmit controller 18 to control the generation of ultrasound signals from the transducer array 6 and hence the images produced by the transducer array and the ultrasound system. The transmit control function of the controller 18 is only one of the functions performed. The controller 18 also takes account of the mode of operation (given by the user) and the corresponding required transmitter configuration and band-pass configuration in the receiver analog to digital converter. The controller 18 can be a state machine with fixed states.

The user interface is also coupled to the multi-planar reformatter 44 for selection and control of the planes of multiple multi-planar reformatted (MPR) images which may be used to perform quantified measures in the image field of the MPR images.

Figure 2:
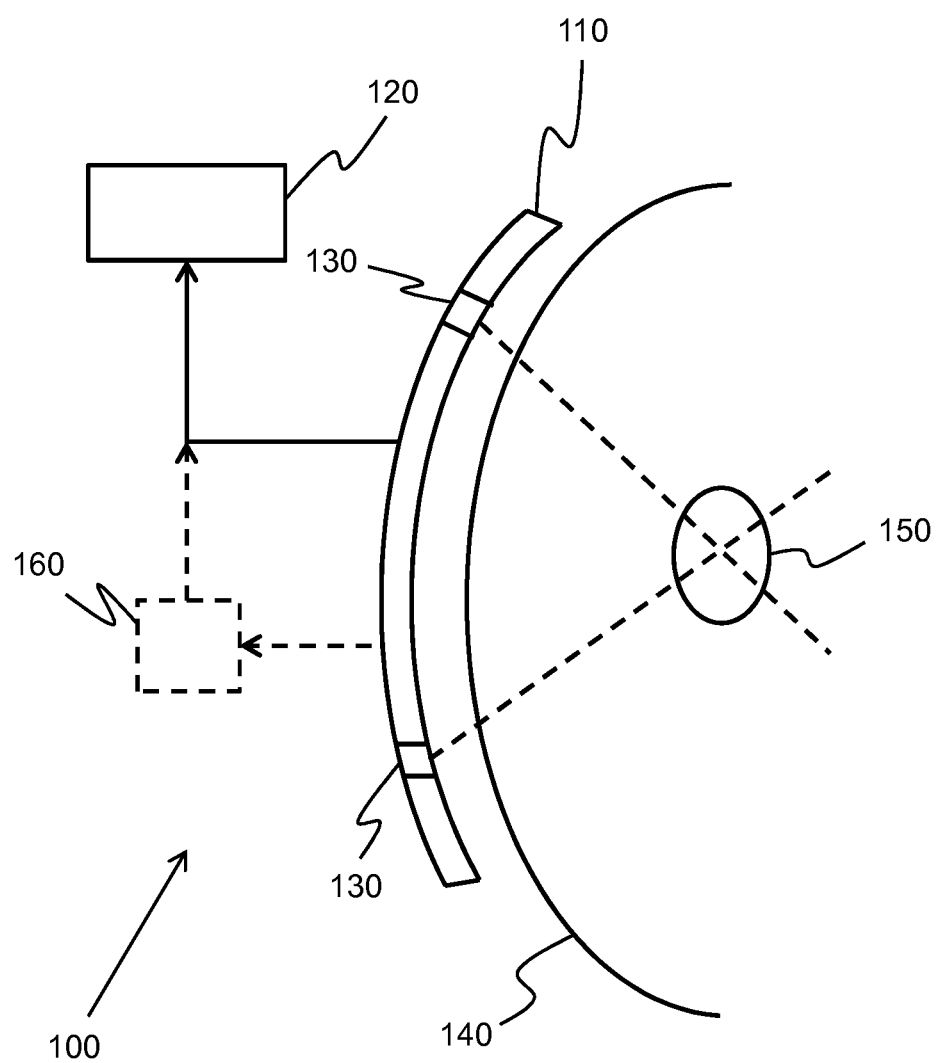
FIG. 2 shows a schematic representation of an ultrasound system according to the invention.

FIG. 2 shows a schematic representation of an ultrasound system 100 comprising an ultrasound transducer array 110 and a processor 120, which may for example be one or more of the processors 26, 28, 30, 34 described above.

The ultrasound transducer array 110 comprises a plurality of transducer elements 130 and is adapted to conform to a subject's body 140. At least two ultrasound transducer elements of the plurality of transducer elements are adapted to acquire a plurality of ultrasound signals from a region of interest 150 at different orientations relative to said region of interest. Each individual transducer element 130 is adapted to transmit and receive ultrasound waves. The transducer elements may comprise piezoelectric transducers or CMUT cells.

The transducer array 110 may be adapted to conform to a subject's body 140 in a number of ways. For example, the plurality of transducer elements may be embedded into a flexible silicone layer.

In other words, the transducer array may be adapted to conform to the body of a subject to ensure that the transducer elements have good contact with the body surface. Further, the material layer positioned underneath the elements, between the transducer elements and the subject, may be selected to have an appropriate acoustic impedance suitable for ultrasound propagation. The transducer array may be made out of any suitable material, for example, by integrating the transducer elements into a fabric or a belt, which could be wrapped around the subject's body.

In addition, the flexible array does not need to be fully closed. For example, the individual elements could be interconnected by any flexible connector piece, which defines the approximate position of the elements with respect to each other.

Alternatively, the individual transducer elements 130 can be attached directly on the skin of the subject in a similar manner to ECG measurement electrodes directly attaching to the skin.

Further, sub-sets of elements (for example, transducer sub-arrays of seven elements) can be placed on a rigid plate, which may then be positioned on the skin. Multiple of these sub-arrays may be used to cover a large area while also following the curvature of the measurement subject.

In the example shown in FIG. 2, the ultrasound system 100 is employed to measure a fetal heartbeat. More specifically, the transducer array 110 is positioned adjacent a maternal abdomen in order to insonify a fetal region.

Due to the fact that the transducer array 100 is flexible and positioned on the maternal abdomen, each transducer element is directed towards the maternal abdomen with a specific angle. Knowing the approximate curvature of the array enables to estimate the location of each sample volume that makes up the 3D ultrasound image captured by the ultrasound system. The approximate curvature of the transducer array may be estimated from the mean curvature of the belly of a pregnant mother.

Alternatively, the ultrasound transducer array 110 may further comprise a sensor 160 and the processor 120 is adapted to determine a curvature of the ultrasound transducer array based on an output of the sensor. The sensor may comprise one or more of: a strain gauge; an accelerometer; a piezoelectric sensor; and a camera. For example, a camera may be used to determine the curvature of the array and, in addition, also the position of the array on the maternal abdomen.

The known position of the individual transducer elements in the 2D array and the curvature of this array allows deriving locations of the transducer elements with respect to the patient and thereby estimating the x- and y-position of the heart location within the measurement volume.

The processor 120 is adapted to receive the ultrasound echo signals acquired by the ultrasound transducer array. Upon receipt of the signals, the processor is adapted to partition the signals according to a signal depth. The partitioning of the signals is further described below with reference to FIG. 3.

Figure 3:
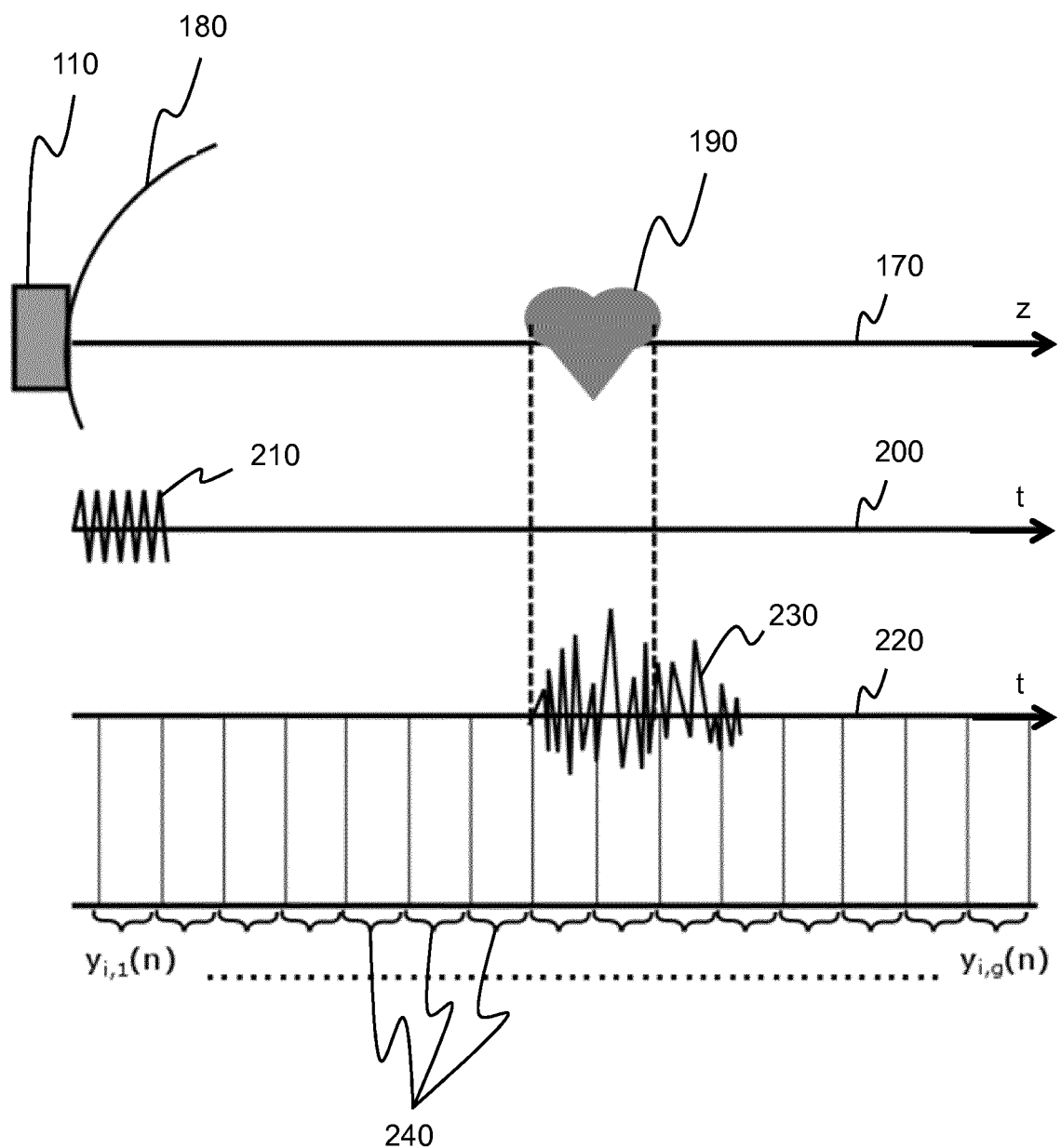
FIG. 3 shows a schematic representation of the partitioning of the received echo signals.

FIG. 3 shows a schematic representation of the partitioning of the received echo signals. The first axis 170 shows a displacement, z, between a transducer array 110 as described above, placed adjacent to a maternal abdomen 180, and a fetal heart 190.

The second axis 200 shows an example ultrasound signal 210 that may be generated by the ultrasound transducers of the transducer array. The second axis corresponds to the first axis proportionally to the speed of the ultrasound signal in the tissue.

The third axis 220 shows the received ultrasound echo signals 230 reflected by the fetal heart 190. A similar signal is received by each active transducer element of the transducer array. The received signal is then partitioned by time gates 240.

Making use of the multiple time gates 240 to partition the received echo signal allows for the estimating the depth (z-position) of the heart locations within the measurement volume.

For each transducer element, multiple Doppler signals are computed from different depths. In other words, for each ultrasound signal partition, a Doppler power is calculated. This may be done by setting multiple time gates, also referred to as range gates, during the Doppler power calculation process. For each transmitted ultrasound burst, one sample n of the received ultrasound echo signal $y_{i,g}(n)$ is obtained, where i denotes the element index and g denotes the range gate index as shown in FIG. 3. For each range gate, a common Doppler processing scheme may be used. The total number of acquired Doppler signals is therefore a product of i*g.

The calculating of the Doppler power may comprise calculating a Doppler signal based on the ultrasound signal partition and calculating a mean squared value for the Doppler signal over a predetermined time period, thereby calculating the Doppler power.

In other words, for each partition of the received echo signal 230, a Doppler signal is computed. The length of this computed Doppler signal is dependent on the size of the range gate. The mean squared value of the Doppler signal is then calculated over the range gate, which defines a predetermined time period. For example, the time period is greater than or equal to 1 second, for example greater than or equal to 2 seconds.

Put another way, in an example the power of each Doppler signal is computed using the mean squared value over a time period of 2 seconds to guarantee that a heartbeat is always measured. The Doppler Power, $P_{i,g}$, reflects the total motion within a specific sample volume. The range gate index determines the depths of the sample volume and the shape of the transmitted ultrasound beam determines the width of the sample volume.

Thus, by noting the range gate index of a detected motion it is possible to identify a depth of a fetal heartbeat based on the Doppler power of each ultrasound signal partition.

The identifying of the depth of the fetal heartbeat may include comparing the Doppler power to a threshold power. In other words, by identifying Doppler powers over a given threshold, the background motion of the imaging area, for example the maternal abdomen, may be discounted. Thus, the fetal heartbeat may be isolated within one or more range gates, thereby identifying the sample volumes in which the fetal heart is located.

The identifying of the depth of the fetal heartbeat may further include clustering the Doppler power values above the threshold power. An automated clustering provides for the separating of the Doppler sources spatially within the measurement volume thereby providing for automated detection of a fetal heart rate and/or location. In an example, the clustering may be performed by way of a two-component Gaussian mixture model.

After thresholding the Doppler power values, all sample volumes that are candidate volumes suitable for measuring a fetal heartrate and, given the estimated curvature of the transducer array, the locations of said sample volumes can be identified. A Gaussian mixture model assumes that the data (the sample volume locations) comes from a Gaussian distribution. As it is known that, in the example of measuring twin heartrates, there are two fetal hearts within the measurement volume, the data is fitted to a two component Gaussian model. The fitted two component Gaussian model can subsequently be used to decide to which cluster, or in other words to which fetal heart, the sample volume belongs.

In a further example, the clustering may be performed by way of a k-means clustering model.

In k-means clustering, there is no underlying assumption of how the sample volume locations are distributed. The k-means algorithm aims to partition the data into k subsets with minimum variance.

Various alternate clustering methods may be employed. For example, hierarchical clustering methods allow grouping of the data without the need to pre-specify the number of clusters to be produced. In the presence of maternal arteries within the sample volume, these clustering methods might be useful and may be employed.

The identified depth of the fetal heartbeat and the location of the at least two ultrasound transducers may then be used to identify the location of the fetal heart.

Figure 4:
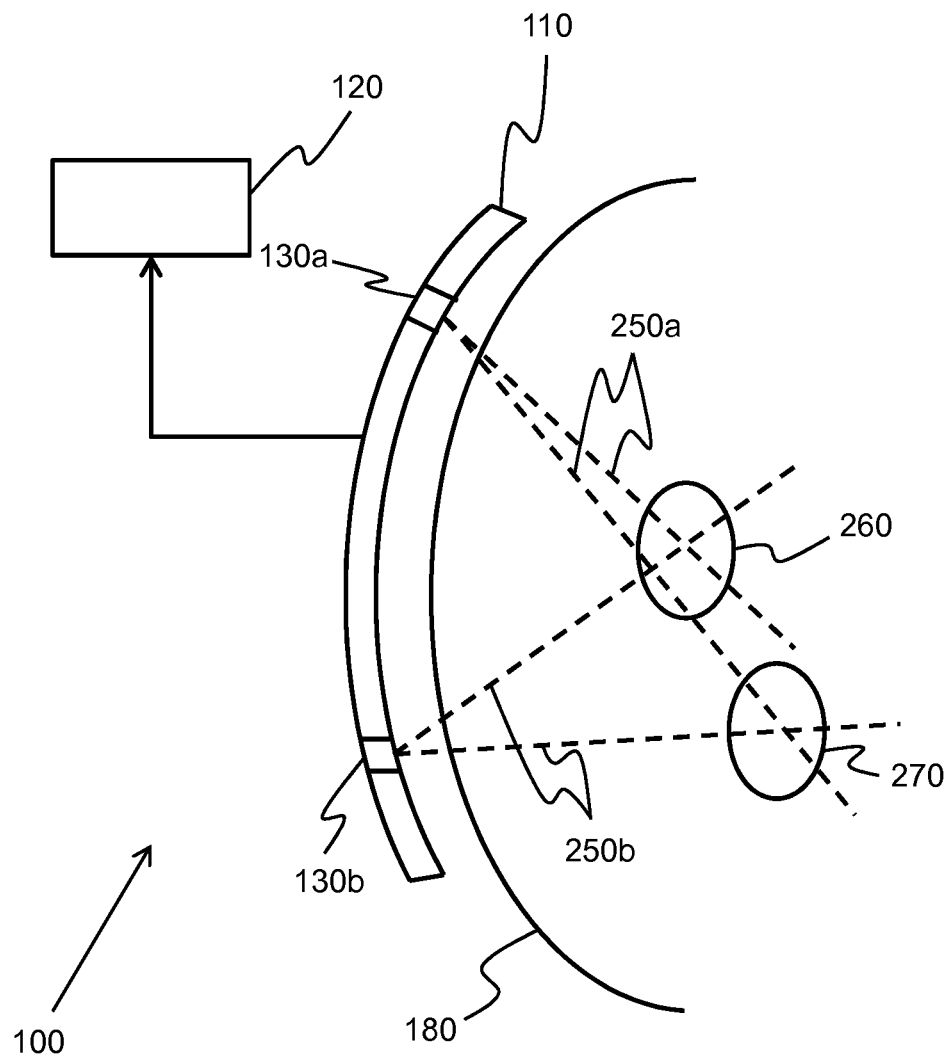
FIG. 4 shows a further schematic representation of an ultrasound system according to the invention.

FIG. 4 shows a schematic representation of the ultrasound system described above applied to a maternal abdomen 180 containing twins. In other words, there are two fetal heartbeats located within the imaging region.

As shown in FIG. 4, the ultrasound signals 250a generated by a first transducer 130a partially intersect both the first fetal heart 260 and the second fetal heart 270. Accordingly, the received echo signals along these transmit lines will contain movement signals from both fetal hearts. This causes a large amount of noise in the received signals and lowers the accuracy of the identified location of the fetal hearts.

Typically, this is addressed by providing multiple ultrasound probes, each directed to imaging one of the fetal hearts. The positioning of two separate ultrasound probes on the maternal abdomen for fetal heart rate monitoring of twins is challenging.

For instance, when both hearts lie in the sample volume of one probe, the measured Doppler signal reflects the motion of both hearts. The Doppler signal therefore shows multiple peaks and the algorithm used to estimate the fetal heart rate, for example an autocorrelation function, will not be able to determine the correct inter-beat intervals of the respective fetuses.

Further, the heart locations of both fetuses may change over time meaning that a repositioning of the ultrasound transducers may be required. In addition, care needs to be taken to unambiguously assign a measured heart rate to the correct fetus. It may occur that the heart rates are incorrectly assigned. If a recorded heart rate trace then looks suspicious it might lead to the wrong interventions being chosen by the clinician.

If the measured heart rates coincidentally coincide, or fall in the same range, the monitoring system may give an alarm as it is not able to determine whether it really measures the heart rate of both fetus or the heart rate of the same fetus twice.

By employing a single flexible transducer array that is adapted to conform to the subject's body, it is possible insonify both fetal hearts with ultrasound signals 250a and 250a generated by a first transducer element 130a and a second transducer element 130b respectively, of the same transducer array 110, from different angles. Thus, it is possible to triangulate the locations of both fetal hearts using at least one unobstructed ultrasound transmit line. In this way, it is possible to accurately isolate each fetal heart location from the remaining received echo signals, thereby increasing the accuracy of the overall identification of the fetal heart regions.

As the transducer array may contain any number of transducer elements, each adapted to transmit and received ultrasound signals, it is likely that at least one signal will be uninterrupted by another Doppler source (such as another fetal heart).

Further, instead of transmitting with all transducer elements simultaneously, only a group (1 or more elements with a predefined apodization profile) of elements which are directed towards the fetal hearts may be activated for transmission to reduce the total amount of acoustic dose delivered to a fetus.

Similarly, instead of receiving with all elements simultaneously, only a group (1 or more elements with a predefined apodization profile) of elements which are directed towards the fetal hearts could be activated for receiving to improve the signal-to-noise ratio of the received echo signals.

Figure 5:
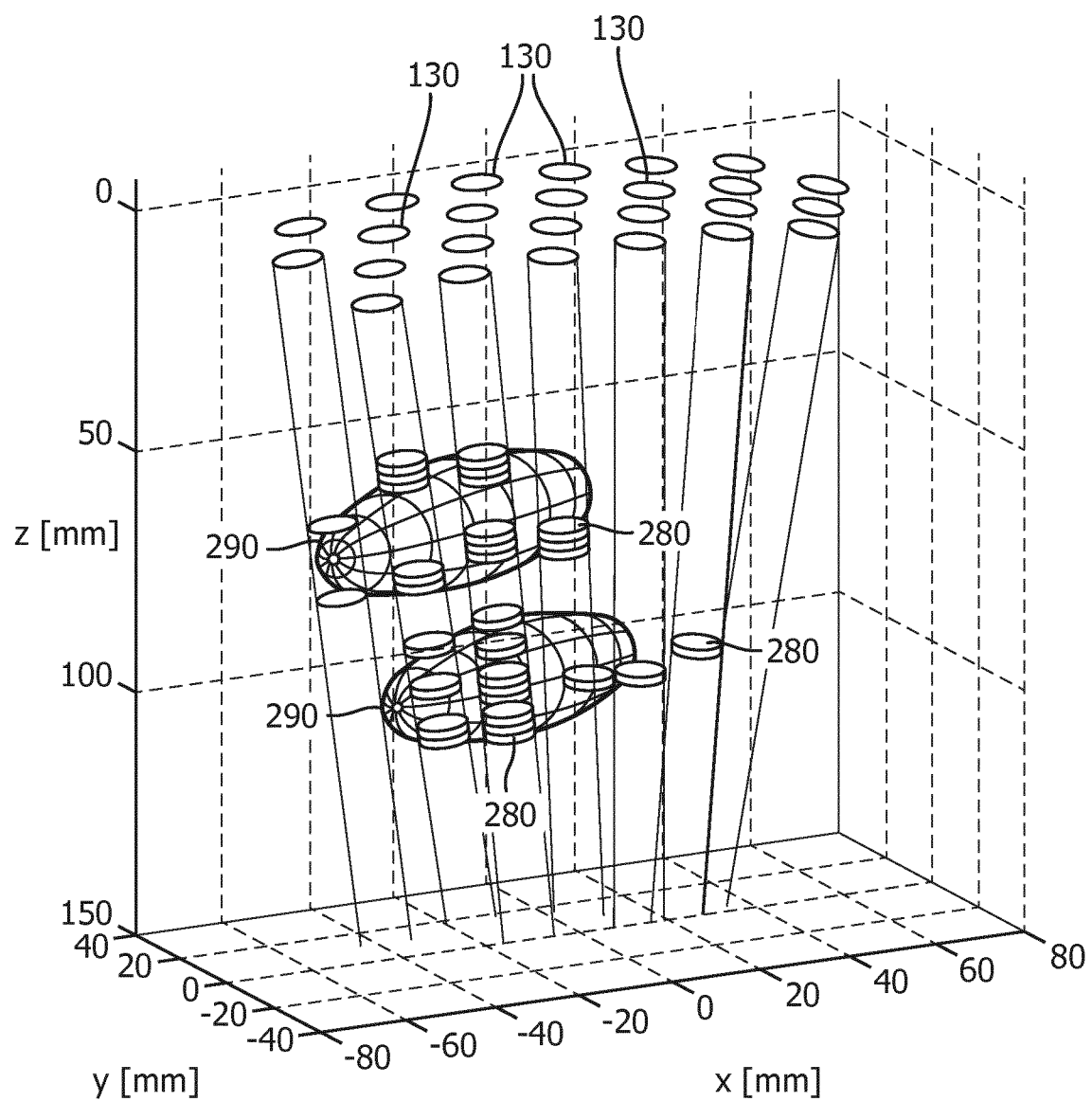
FIG. 5 shows a 3D visualization of the sample volumes of a measurement region containing two fetal hearts.

FIG. 5 shows a 3D visualization of the sample volumes of a measurement region containing two fetal hearts. FIG. 5 shows an array of ultrasound transducer elements 130 positioned above a measurement region defined by the x, y and z axes. Within the measurement volume, sample volumes 280 are shown, which represent received echo signal partitions with a calculated Doppler power above the predetermined threshold. The darker the represented sample volume, the higher the Doppler power measured there i.e. the more movement in this area.

The Doppler powers measured across the transducer array may then be clustered and used to identify the fetal heart regions 290.

Put another way, the Doppler power, Pi,g, can be visualized in 3D to show where the strongest Doppler signals are located. Visualization of the Doppler power in 3D provides for simple confirmation of whether there are only two Doppler sources in the measurement volume, or if for example a pulsating maternal artery is present within the measurement volume. In particular, maternal arteries may lie in the sample volume of the ultrasound transducers and may corrupt the acquired Doppler signal. This may lead to erroneous registration of the fetal heart rates or a measurement of the maternal heart rate instead. In this case, the system proposed above may identify such sources of erroneous Doppler signals and discount them in the fetal heart signals.

In an example, all sample volume locations with Doppler power, Pi,g, above a predetermined threshold are fitted to a two-component Gaussian mixture model and, subsequently, clustered. The median fetal heart rate is then computed from the Doppler signals of each cluster to obtain two fetal heart rate measurements.

Such a 3D visualization may be presented to a user by way of an appropriate display, wherein the display is adapted to show the fetal heart region to a user.

The example shown in FIG. 5 was obtained using a transducer array having 25 transducer elements. The Doppler signals were calculated from 64 range gates. For experimental validation, a twin-fetal heart in-vitro setup was used to test the system. The results confirm that a single flexible sensor matrix can enable localization and visualization of twin fetal hearts. With the proposed clustering algorithm, the two fetal heart rates can be detected without the aforementioned problems of manually positioning two ultrasound transducers. This may lead to improved clinical workflow and better fetal health monitoring in twins.

Figure 6:
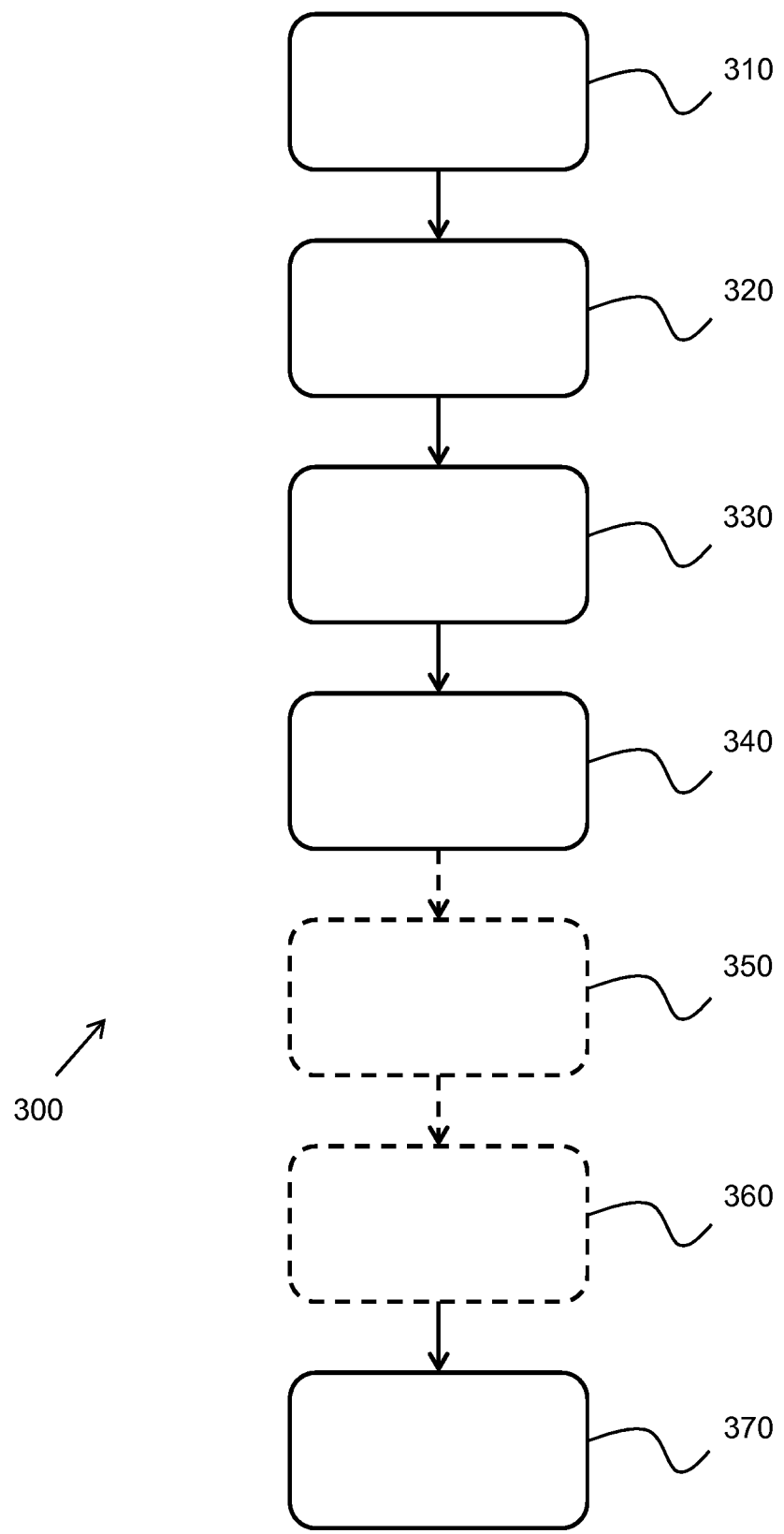
FIG. 6 shows a method of the invention.

FIG. 6 shows an ultrasound imaging method 300 according to the invention.

In step 310 a plurality of ultrasound signals are acquired by way of at least two ultrasound transducers having different orientations to a region of interest.

In step 320, the plurality of ultrasound signals are partitioned according to a signal depth, for example, by way of range gates.

In step 330, a Doppler power is calculated for each ultrasound signal partition.

In step 340, a depth of a fetal heartbeat is identified for each ultrasound signal based on the Doppler power of each ultrasound signal partition.

In step 350, the Doppler power may be compared to a threshold power and in step 360 the Doppler power values above the threshold power may undergo clustering.

In step 370, a fetal heart region is identified based on the identified fetal heartbeat and a location of the at least two ultrasound transducers.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. An ultrasound system, the system comprising:
an ultrasound transducer array, wherein the ultrasound transducer array comprises a plurality of transducer elements, adapted to conform to a subject's body, wherein at least two ultrasound transducer elements of the plurality of transducer elements are adapted to acquire a plurality of ultrasound signals from a region of interest at different orientations relative to said region of interest; and
a processor adapted to receive the plurality of ultrasound signals acquired by the ultrasound transducer array, wherein the processor is adapted to:
partition the plurality of ultrasound signals according to a signal depth so as to generate ultrasound signal partitions;
for each ultrasound signal partition, calculate a Doppler power;
identify depths of twin heartbeats based on the Doppler power of each ultrasound signal partition; and
identify fetal heart regions based on the depths of the twin heartbeats and a location of the at least two ultrasound transducers,
wherein to identify the depths of the twin heartbeats, the processor is adapted to compare the Doppler powers to a threshold power,
wherein to identify the depths of the twin heartbeats, the processor is adapted to cluster first Doppler powers of the Doppler powers above the threshold power, and
further wherein to cluster the first Doppler powers, the processor is adapted to fit locations of the first Doppler powers to a two-component Gaussian mixture model to execute automated detection of twin heart rates associated with the twin heartbeats and twin heart locations associated with the twin heartbeats.

2. The ultrasound system as claimed in claim 1, wherein the calculation of the Doppler power comprises:
calculating Doppler signals based on the ultrasound signal partitions; and
calculating a mean squared value for each of the Doppler signals over a predetermined time period, thereby calculating the Doppler powers.

3. The ultrasound system as claimed in claim 2, wherein the time period is greater than or equal to 1 second.

4. The ultrasound system as claimed in claim 1, wherein the processor is further adapted to calculate one or more median fetal heart rates based on one or more of the twin heart rates.

5. The ultrasound system as claimed in claim 1, wherein the system further comprises a display, wherein the display is adapted to show the fetal heart regions to a user.

6. The ultrasound system as claimed in claim 5, wherein the processor is further adapted to determine a location for each ultrasound signal partition within the region of interest, and wherein the display is further adapted to show the fetal heart regions in relation to each ultrasound signal partition.

7. The ultrasound system as claimed in claim 1, wherein the ultrasound transducer array further comprises a sensor and the processor is further adapted to determine a curvature of the ultrasound transducer array based on an output of the sensor.

8. The ultrasound system as claimed in claim 7, wherein the sensor comprises one or more of:
- a strain gauge;
- an accelerometer;
- a piezoelectric sensor; and
- a camera.

9. The ultrasound system as claimed in claim 1, wherein the at least two ultrasound transducers comprise one or more of:
- piezoelectric transducers; and
- CMUTs.

10. An ultrasound imaging method, the method comprising:
- acquiring, by way of at least two ultrasound transducers having different orientations to a region of interest, a plurality of ultrasound signals;
- partitioning the plurality of ultrasound signals according to a signal depth so as to generate ultrasound signal partitions;
- for each ultrasound signal partition, calculating a Doppler power;
- identifying depths of of twin heartbeats based on the Doppler power of each ultrasound signal partition;
- comparing the Doppler powers to a threshold power;
- clustering first Doppler powers of the Doppler powers above the threshold power, wherein the clustering includes fitting locations of the first Doppler powers to a two-component Gaussian mixture model to execute automated detection of twin heart rates associated with the twin heartbeats and twin heart locations associated with the twin heartbeats; and
- identifying fetal heart regions based on the depths of the twin heartbeats and a location of the at least two ultrasound transducers.

11. A non-transitory computer-readable medium storing computer program code which is adapted, when said computer program code is run on a computer, to implement the method of claim 10.

* * * * *